United States Patent [19]

Lindgren et al.

[11] Patent Number: 4,944,361
[45] Date of Patent: Jul. 31, 1990

[54] ACOUSTIC EAR MUFF

[75] Inventors: Mats E. G. Lindgren, Vikmanshyttan; Ingvar S. Sjöovist, Sorunda, both of Sweden

[73] Assignee: A.B. Kompositprodukter S.K.-F.M., Vikmanshyttan, Sweden

[21] Appl. No.: 237,040

[22] Filed: Aug. 29, 1988

[30] Foreign Application Priority Data

Sep. 2, 1987 [SE] Sweden .................. 8703414

[51] Int. Cl.⁵ .................. A42B 1/06; G10K 11/00
[52] U.S. Cl. .................. 181/129; 2/209; 2/423
[58] Field of Search .................. 181/129, 130; 381/183; 2/203, 208, 209, 423

[56] References Cited

U.S. PATENT DOCUMENTS

| | | | |
|---|---|---|---|
| 3,430,261 | 3/1969 | Benner | 2/209 X |
| 3,661,225 | 5/1972 | Anderson | 181/175 |
| 3,944,018 | 3/1976 | Satory | 181/129 X |
| 4,069,512 | 1/1978 | Palmaer | 2/209 |
| 4,104,743 | 8/1978 | Bottger | 2/423 |

Primary Examiner—Benjamin R. Fuller
Attorney, Agent, or Firm—Sughrue, Mion, Zinn, Macpeak, and Seas

[57] ABSTRACT

An acoustic ear muff includes a pad or cup (2) which is made of rigid material and incorporates an opening for receiving one ear of the wearer, and a resilient sealing annulus (10) intended for abutment with the head of the wearer, and also resilient pressure-exerting means (5) connected to the shell of a protective helmet (1), a head strap or like head gear. The ear muff provides good acoustic damping and a high degree of comfort, owing to the fact that the resilient pressure-exerting means is configured to produce a low pressing force substantially independently of head sizes which vary within given limits. The pressure-exerting means includes, to this end, a spring element in the form of a combined torsion and bending spring.

11 Claims, 3 Drawing Sheets

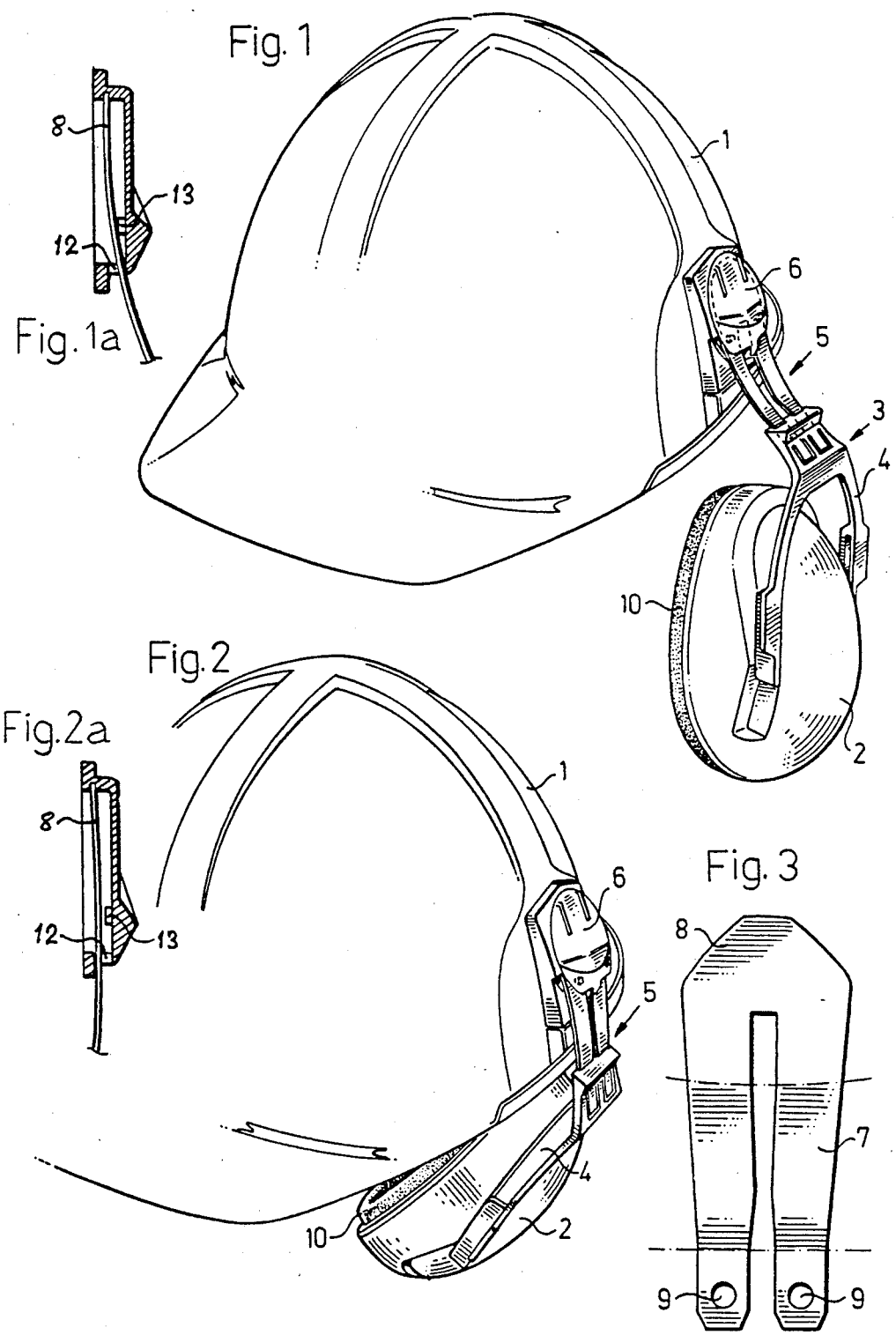

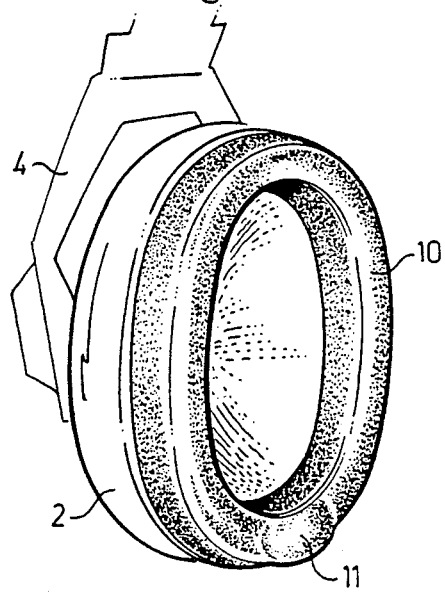
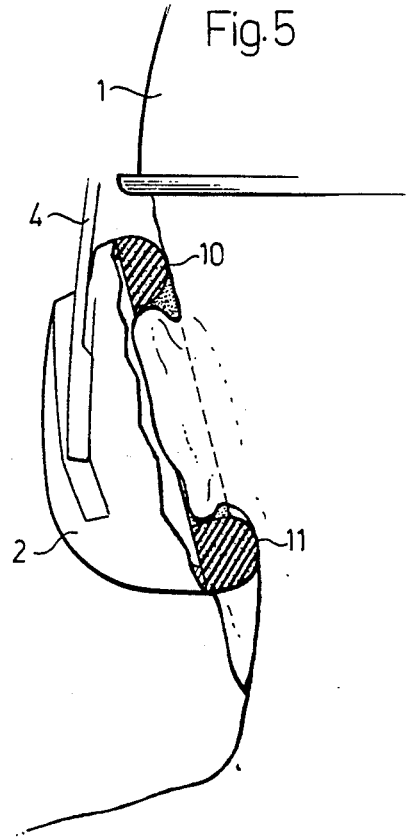

ACOUSTIC EAR MUFF

BACKGROUND OF THE INVENTION

The present invention relates to an acoustic ear muff of the kind which includes a pad of rigid material which has provided therein an opening for accommodating one ear of the wearer and an elastic sealing annulus which is located around the edge of the opening and intended for abutment with head of said wearer, and which ear muff further includes a sprung pressing means attached to the shell of a protective helmet, to a head strap or to like head gear.

Persons who stay in noisy environments for any length of time need some form of protection against the noise. Such protective devices often have the form of ear muffs carried on a protective helmet, such as those worn by forestry workers and mine workers, and by people working on building or construction sites, ship building yards, and like locations.

Two requirements can be placed on an effective acoustic ear muff, i.e. the ability of the ear muff to dampen noise and its capability of being worn comfortably. These two requirements, however, are mutually counterproductive in the main and cannot both be fulfilled satisfactorily in practice at one and the same time. For example, in order to afford a good sound damping effect, if must be possible to hold the ear muff tightly against the head, so as to eliminate the presence of noise-leaking pasageways between the sealing annulus of the ear muff and the head. When worn tightly on the head, however, the ear muff will cause discomfort and even pain, and may also give rise to a rash or the like in the contact area. From the aspect of comfort, the force with which the ear muff is pressed against the head shoulder be as small as possible, which results in poor acoustic damping, however.

Tests have shown that if, whilst in a noisy environment, it is necessary to remove the ear muff for as long as 10% of the total period which the person concerned remains in the area, the risk of damage to the hearing is no smaller than if no ear muff were worn at all.

Hearing damage is likely even when the ear muff is removed for a period as short as 3% of the total period, and a period as short as 1% of the total period results in a marked impairment in the overall protection afforded by the ear muff. The conclusion to be drawn from this is that it is not worthwhile to strive for the best possible acoustic damping effect if the price to be paid is that of comfort, so that the wearer is forced to remove the ear muffs during his presence in a noisy environment.

Prior known acoustic ear muffs available commercially have normally been so constructed as to provide good acoustic damping with head sizes above a given minimum size and a good degree of comfort with sizes beneath a given maximum size. In the case of large heads, the ear muffs lie too tightly against the head and are therefore less comfortable, whereas in the case of small heads the force with which the ear muffs bear against the head is much too small to achieve good acoustic damping. The difference in the force with which the ear muffs are pressed against the head, hereinafter referred to as the pressing force, can vary by 300% between small and large heads. Ear muffs are to be found which can be adjusted to different head sizes. These adjustable ear muffs, however, have not been found satisfactory.

SE-B-7904611-6 teaches an ear-muff attachment device which, in an attempt to achieve a substantially constant pressing force, uses a cup spring and an arm which co-acts with the convex side of the spring. This embodiment also has certain drawbacks.

SUMMARY OF THE INVENTION

The main object of the present invention is to provide an improved acoustic ear muff which will afford good acoustic damping in combination with a high degree of comfort for varying head sizes. The force with which the ear muff is pressed against the head, i.e. the pressing force, shall be substantially constant for head sizes which vary between a minimum value and a maximum value. This value may vary by about 40 mm between 130-170 mm with regard to the width of the head, measured between the orifices of the auditory meatus.

In accordance with the present invention, an acoustic ear muff of the kind mentioned in the introduction is characterized in that the sprung pressing means is configured to produce a low pressing force which is essentially independent of varying head sizes within given limits; and in that the pressing means includes to this end a spring element in the form of a combined torsion and bending spring.

Because the pressing force can be kept low, such as acoustic ear muff will provide good acoustic damping combined with a high degree of comfort. This will enable the ear muffs to be worn continuously, so as to provide optimum protection against damage to the hearing.

The spring element will preferably comprise a substantially U-shaped leaf spring, the free ends of the legs of which are biased towards one another in the plane of said legs, in order to twist the same to some extent. The base part of the spring element may be secured in a slot which has arranged therein spring-co-acting projections which determine the extent to which the legs are twisted and therewith the characteristic of the spring.

In the case of one preferred embodiment of the invention, the sprung pressing means is connected to the pad by means of a bifurcate holder, the legs of which are pivotally connected to the pad. The free ends of the spring legs can therewith be fastened at a given mutual distance apart in a slot provided in the central part of the bifurcate holder.

In the case of an ear muffs, or ear muffs, intended to be fitted to a protective helmet or the like, the spring element will conveniently have two stable positions, such that in one position the ear muff can be pressed against the head with a small and substantially constant force sufficient to hold the ear muff tightly against the head, and in the second position is spaced from the ear.

In order to prevent the sealing annulus from becoming soiled and deformed as a result of contact with the protective helmet, the spring element is preferably connected to the helmet in a manner such that when rotating the ear muff to a rest position located adjacent the helmet the ear muff is unable to take that position of the two possible stable positions in which the ear muff abuts the head.

In the case of an acoustic ear muff which is intended to be fitted to a head strap or like head gear, the aforesaid spring element will preferably have two functional positions, such that in one position the ear muff is pressed against the head with a small and substantially constant force sufficient to hold the ear muff tightly against the head, and in the second position abuts the head with a still smaller force intended solely for retention of the head strap.

In accordance with one preferred embodiment, the sealing annulus has an outwardly projecting part which is intended to fill the cavity adjacent the rear edge of the cheek bone, and the spring element is configured to exert a spring force so adapted that the remaining part of the sealing annulus will only be slightly compressed.

BRIEF DESCRIPTION THE DRAWINGS

The invention will now be described in more detail with reference to the accompanying drawings.

FIG. 1 illustrates a protective helmet provided with an acoustic ear muff according to the invention, said ear muff being shown in an inoperative position. FIG. 1a illustrates a detailed sectional view of a portion of the ear muff in the inoperative position.

FIG. 2 illustrates the helmet shown in FIG. 1, with the ear muff in its operative position. FIG. 2a illustrates a detailed sectional view of a portion of the ear muff in the inoperative position.

FIG. 3 illustrates the spring element used with the inventive ear muff.

FIG. 4 illustrates the pad and sealing annulus of the inventive ear muff.

FIG. 5 illustrates schematically the pad shown in FIG. 4 in its operative position.

DETAILED DESCRIPTION OF THE PREFERRED EMBODIMENT

Figure 6:
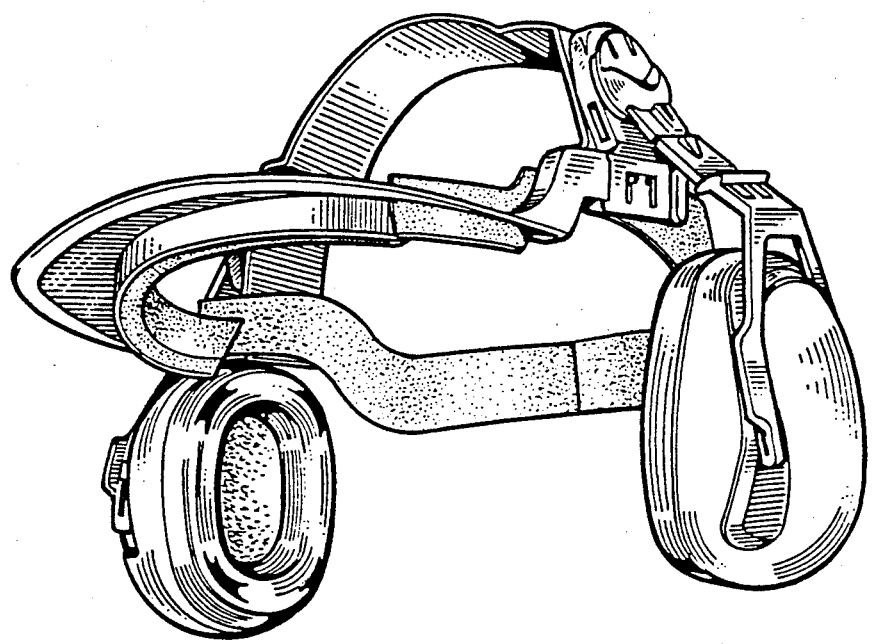
FIG. 6 illustrates a head strap provided with an acoustic ear muff according to the invention.

FIGS. 1 and 2 illustrate a conventional protective helmet 1 which has an acoustic ear pad 2 connected thereto. The pad 2 is attached to the helmet by means of a bifurcate holder arrangement 3 which can be displaced linearly in relation to the pad and the legs 4 of which are pivotally mounted on the pad 2. The central part of the holder 3 is connected, via a spring element 5, with a further holder 6 rotatably mounted on the helmet. The spring element 5 has a bistable function, i.e. when bent the spring element will transfer quickly from one stable, functional position to another stable functional position, as illustrated in FIGS. 1 and 2.

FIG. 1 shows the acoustic ear pad 2 spaced from the ear, whereas FIG. 2 shows the pad pressed against the ear with a small force. This force shall be substantially constant for head sizes varying within a given range. In the development of an arrangement according to the invention, it has been endeavoured, and achieved, to hold this force substantially constant within a range of 130–170 mm, measured between the orifices of the auditory meatus. It is possible to maintain a pressing force of from 7–9N and most often between 7.5–8.5N within this size range. This compares favourably with conventional acoustic ear muffs, which in the case of large head sizes can exert a pressing force greater than 12N and in the case of small heads lower than 4N. The lower force exerted by the known acoustic ear muffs results in poor acoustic damping, whereas the high pressure force results in too much discomfort for the pads to be worn continuously.

In the case of the illustrated embodiment, the substantially constant pressing force in combination with a bistable spring characteristic is achieved with the aid of a spring element 5 which consists of a combined bending and torsional spring, which in the FIG. 3 embodiment has a substantially U-shaped configuration and comprises two legs 7 and a base part 8.

By biasing the free ends of the legs 7 towards one another in the plane of the legs, i.e. by reducing the mutual distance between the legs, the legs will be slightly twisted or rotated and either take a concave position, illustrated in FIG. 1, or a convex position, illustrated in FIG. 2. The base part 8 of the spring element is held in a slot in the holder 6, said slot being provided with two projections 13 which lie against respective legs at their junction with the base part 8. The extent to which the legs are rotated in the slot, and therewith the value of the spring characteristic, is determined by the length of said projections. The free ends of the legs 7 are biased towards one another in a slot provided in the holder 3, said legs being provided with holes 9 which are fitted over pegs (not shown) mounted on the holder 3, said pegs determining the degree of bias on the legs 7.

The illustrated spring element obtains a bistable function, simply due to the fact that the spring is subjected to both rotation and bending, which from the aspect of force and torque are directed towards one another. The resultant forces balance one another in the two stable positions. One significant advantage afforded by a spring element according to the invention, however, is that it will produce a substantially constant pressing force over a relatively large bending range, in accordance with the aforegoing.

As illustrated in FIGS. 1a and 2a, the base part 8 of the spring element 5 is secured in a slot 12 of the holder 6. The holder 6 has projections 13 provided in the slot 12. The projections 13 coat with the spring to determine the extent of twist of the legs and the spring characteristics thereof.

The extent to which the legs 7 can rotated can be restricted by appropriate selection of the length of the projections 13 on the holder 6, such that there is obtained only one stable position corresponding to the position in which the ear muffs lie against the head. However, when bending out the ear muff a point is reached at which the force required to continue this outward bending of the ear muff suddenly decreases without the spring element moving into a further stable position. This construction is suitable for use together with a head strap, wherewith the said outer position can be utilized as a rest position since sufficient pressing force still remains to hold the head strap, or head stirrup, firmly.

However, in order to ensure that the constant low pressing force generated in the operative position of the acoustic ear muff will be sufficient to achieve good acoustic damping, the sealing annulus 10 arranged around the edge of the pad, or cup, 2, must be configured so as to lie completely against the head even in the case of the low pressing force. Consequently, as illustrated in FIG. 4, the sealing annulus 10 of the illustrated embodiment has an outwardly projecting part 11 which is located opposite the cavity located behind the ear in the region of the rearward edge of the jawbone, so as to fill this cavity without requiring appreciable deformation of the remainder of the sealing annulus.

FIG. 5 illustrates that the projection 11 will completely fill the cavity, without the remainder of the annulus 10 being appreciably deformed. This is one requisite for ensuring that satisfactory acoustic damping can be achieved with a low pressing force. In distinction with the inventive acoustic ear muff, the earlier known ear muffs require a relatively high pressing force in order to deform the greater part of the sealing annulus so that said annulus will enter and fill said cavity. With regard to comfort, the sealing annulus 10 according to the invention will suitably be made of a foamed plastic material covered with a moisture impervious casing.

The holder 6 of the illustrated embodiment can be rotated in a manner to pivot the acoustic ear muff to a rest position adjacent the helmet. In this regard, the holder is configured in a manner which prevents the spring element from being bent back from the position illustrated in FIG. 1 to the second stable position subsequent to such rotation of the holder 6. This prevents the ear muff and the sealing annulus 10 from coming into contact with the outer surface of the helmet, such contact being possible in the case of the earlier known ear muffs. Such contact is unsuitable, since the outer surfaces of the helmet are often dusty, dirty or covered with resinous particles and contact with the surfaces is liable to contaminate the sealing ring 10. Furthermore, the sealing annulus may be permanently deformed if held pressed against the helmet for long periods of time. These problems are eliminated through suitable attachment of the spring element according to the invention.

A preferred embodiment of an inventive acoustic ear muff for reducing the effect of sound on the ears has been described in the aforegoing. It will be understood, however, that the illustrated embodiment can be modified in several respects within the scope of the following claims. For instance, as illustrated in FIG. 6, the acoustic ear muff can be attached to a head strap 14 in the same manner that it is attached to a protective helmet. Also that the illustrated ear muff arrangement can also be applied to the earphones of audio equipment. Thus, modifications can be made to the attachement means, holders and the like. The spring element can be given any suitable, precise geometric configuration and the sealing annulus any suitable profile.

We claim:

1. An acoustic ear muff including a pad or cup (2) made of a rigid material and incorporating an opening for accommodating an ear of a wearer, and a resilient sealing annulus (10) which is located around a defining edge of said opening and which is intended to be brought into abutment with a head of the wearer, and further includes spring pressure exerting means (5) connected to a shell of a protective helmet (1) or to a head strap, characterized in that the spring pressure-exerting means is configured to produce a low pressing force which is substantially independent of head sizes which vary within given limits and in that the pressure exerting means includes a spring element (5), said spring element comprising a pair of elongate leaf spring having legs spaced apart from one another, one end of each of said leaf spring legs being secured to said shell while the other end of each of said spring legs are biased towards one another in a plane of said springs so as to impart a given twist thereto.

2. An acoustic ear muff according to claim 1, characterized in that a base part (8) of the spring element (5) is secured in a slot, and in that the slot has provided therein projections which co-act with the spring and which determine the extent of twist of the legs (7) and spring characteristic.

3. An acoustic ear muff according to claim 2, characterized in that the spring element (5) is connected to the pad or cup (2) by a bifurcate holder (3) which is pivotally connected to the pad or cup (2).

4. An acoustic ear muff according to claim 3, characterized in that free ends of the legs (7) of the leaf spring (5) are secured in a given mutually spaced relationship in a slot in a central part of the bifurcate holder (3).

5. An acoustic ear muff according to claims 1 or 2 characterized in that, as a result of said twist, said spring element (5) has two stable positions; and in that in a first position of said spring element the muff is pressed against the head with a small and substantially constant force sufficient to achieve tight abutment between muff and head, and in a second position is spaced from the ear of the wearer.

6. An acoustic ear muff according to claim 5, characterized in that the spring element (5) is attached to the helmet in a manner such that when the ear muff is disposed at a rest position adjacent said helmet the spring element is unable to move to said first position.

7. A acoustic ear muff according to claims 1-3 or 2, characterized in that said spring element (5) has two functional positions, and in that in a first position the ear muff is pressed against the head with a small but substantially constant force sufficient to achieve tight abutment of the ear muff with the head, and in a second position abuts the head with a still smaller force intended solely for retention of the head strap.

8. An acoustic ear muff according to claims 1 or 2, characterized in that the sealing annulus (10) has provided thereon an outwardly projecting part (11) which is intended to fill a cavity located adjacent a rear edge of a jawbone, and in that the spring element (5) is configured to generate a spring force such that a remaining part of the sealing annulus will be only slightly compressed.

9. An acoustic ear muff according to claim 5, characterized in that the sealing annulus (10) has provided thereon an outwardly projecting part (11) which is intended to fill a cavity located adjacent a rear edge of a jawbone, and in that the spring element (5) is configured to generate a spring force such that a remaining part of the sealing annulus will be only slightly compressed.

10. An acoustic ear muff according to claim 7, characterized in that the sealing annulus (10) has provided thereon an outwardly projecting part (11) which is intended to fill a cavity located adjacent a rear edge of a jawbone, and in that the spring element (5) is configured to generate a spring force such that a remaining part of the sealing annulus will be only slightly compressed.

11. The acoustic ear muff of claim 1, wherein said legs of said leaf springs are connected at one end thereof to form a U-shaped leaf spring.

* * * * *